US012599783B2

(12) United States Patent (10) Patent No.: US 12,599,783 B2
Freedman et al. (45) Date of Patent: Apr. 14, 2026

(54) QUALITY ASSURANCE FOR A RADIOTHERAPY DEVICE

(71) Applicant: Elekta Limited, Crawley (GB)

(72) Inventors: Joshua Freedman, Crawley (GB);
David Roberts, Crawley (GB);
Christopher Knox, Crawley (GB)

(73) Assignee: Elekta Limited, Crawley (GB)

( * ) Notice: Subject to any disclaimer, the term of this patent is extended or adjusted under 35 U.S.C. 154(b) by 497 days.

(21) Appl. No.: 18/181,281

(22) Filed: Mar. 9, 2023

(65) Prior Publication Data

US 2023/0310898 A1 Oct. 5, 2023

(30) Foreign Application Priority Data

Mar. 30, 2022 (GB) ..................................... 2204560

(51) Int. Cl.
*A61N 5/10* (2006.01)
(52) U.S. Cl.
CPC ......... *A61N 5/1075* (2013.01); *A61N 5/1049* (2013.01); *A61N 2005/1076* (2013.01)
(58) Field of Classification Search
CPC ................ A61N 5/1075; A61N 5/1049; A61N 2005/1076
See application file for complete search history.

(56) References Cited

U.S. PATENT DOCUMENTS

| | | | |
|---|---|---|---|
| 10,463,885 B2 | 11/2019 | Scheib | |
| 2016/0082284 A1 | 3/2016 | Ooga et al. | |
| 2021/0236855 A1* | 8/2021 | Adamson | A61N 5/1045 |

OTHER PUBLICATIONS

"United Kingdom Application Serial No. 2204560.3, Examination Report dated Sep. 7, 2022", (Sep. 7, 2022), 5 pgs.
Crijns, S. P. M., et al., "Towards MRI-guided linear accelerator control: gating on an MRI accelerator", Physics in Medicine & Biology 56.15, (2011), pp. 4815-4825.
Knutson, Nels C., et al., "Equivalency of beam scan data collection using a 1D tank and automated couch movements to traditional 3D tank measurements", Journal of applied clinical medical physics 19.6, (2018), pp. 60-67.
Sengupta, Saikat, et al., "Continuously moving table MRI with golden angle radial sampling", Magnetic resonance in medicine 74.6, (2015), pp. 1690-1697.
Valdes, Gilmer, et al., "Use of TrueBeam developer mode for imaging QA.", Journal of applied clinical medical physics 16.4, (2015), pp. 322-333.

* cited by examiner

*Primary Examiner* — Nicole M Ippolito
(74) *Attorney, Agent, or Firm* — Schwegman Lundberg & Woessner, P.A.

(57) ABSTRACT

A quality assurance method for a radiotherapy device is disclosed. The method comprises disposing a phantom on a patient couch of the radiotherapy device, moving the patient couch to simulate motion of a subject, determining a measured value associated with the phantom, and comparing the measured value to an expected value. A radiotherapy device is also disclosed, the radiotherapy device comprising a radiation source configured to apply a radiation beam, a patient couch, a phantom disposable on the patient couch, and a controller communicatively coupled to the patient couch. A computer-readable medium storing instructions is also disclosed. A phantom for a radiotherapy device is also disclosed.

20 Claims, 5 Drawing Sheets

400

QUALITY ASSURANCE FOR A RADIOTHERAPY DEVICE

TECHNICAL FIELD

This disclosure relates to quality assurance for a radiotherapy device, and in particular to quality assurance using a phantom.

CLAIM FOR PRIORITY

This application claims the benefit of priority of British Application No. 2204560.3, filed Mar. 30, 2022, which is hereby incorporated by reference in its entirety.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In radiotherapy treatment, it is desirable to deliver a prescribed dose of radiation to a target region of a subject and to limit irradiation of other parts of the subject, i.e. of healthy tissue. Motion of the subject can cause a decreased dose to be applied to the target region and/or an increased dose to be applied to the healthy tissue. To address this, known techniques include monitoring a location of the subject and gating the treatment beam such that radiation is applied only when the subject (i.e. the target region within the subject) is in a desired location and not when the subject/target region is in a suboptimal location. This improves clinical outcomes.

There are various physiological motions that can contribute to a total motion of a subject. Discrete, gross or large-scale movements of a subject may include shifting position, coughing or sneezing. The subject may also undergo cyclical, physiological movement. For example, the subject may undergo respiratory motion due to their breathing cycle. The subject may also undergo cardiac motion based on beating of their heart. These motions can alter the location of a subject and/or of a tumour in a time-dependent manner relative to the respective location of the subject and/or of the tumour at the start of the radiotherapy treatment.

In radiotherapy, commissioning and device acceptance testing (DAT) are required to ensure that an installed radiotherapy device is working as expected. In addition, routine quality assurance (QA) is required to ensure that the device meets the expected tolerances. Such commissioning testing, DAT and periodic QA include geometrical, mechanical and dosimetric testing. A common geometrical and dosimetric test is the end-to-end (E2E) test, which verifies that the final dose delivered is consistent with the dose calculated by a treatment plan.

For conducting such testing, a phantom may be used. A phantom is a substitute for a subject's body or a part of a subject's body. In other words, a beam of radiation may be delivered to a phantom as part of testing to ensure that the beam of radiation can be safely and accurately delivered to a subject, with parameters of the radiotherapy device and the radiation delivery being as expected or intended within given tolerances. The radiation dose received by the phantom can be measured using an ionization chamber, gel dosimeters, a diode detector and/or a dosimetric film. One or more of these may be disposed inside the phantom. Alternatively, one or more of these may be disposed opposite the beam and used to infer the radiation dose at the location of the phantom. A phantom may be used to test a treatment plan. A radiation delivery may be performed in accordance with the treatment plan with the phantom in an intended location of the subject or a part of the subject. The dose actually received by the phantom can be compared to the intended dose according to the treatment plan to verify that the radiation delivery is safe and suitable for applying to the subject. Example phantoms suitable for QA of a radiotherapy device include Delta4, IC Profiler-MR array, PTW 1500 array (PTW, Freiburg, Germany), and ArcCHECK (Sun Nuclear Corporation, Melbourne, FL, USA) phantoms.

Some radiation deliveries account for intrafractional motion of the subject, i.e. motion of the subject during a treatment session. For example, a radiation delivery may account for respiratory motion through gating of the treatment beam when the subject is in a suboptimal location or tracking the beam such that the locations irradiated are varied in accordance with the movement of the subject or a part thereof. Quality assurance of such treatments is more complex than quality assurance of treatments for which the subject, or at least the irradiated part of the subject, is assumed or controlled to be stationary. In other words, because the subject will move during the treatment, a static phantom may not provide an accurate indication of the dose that would be received by the subject or particular locations within the subject.

One approach to managing this issue is to use a respiratory motion phantom, which is capable of changing its dimensions as a function of time in order to replicate respiratory motion of a subject. However, such respiratory motion phantoms are expensive and involve significant engineering complexity. In addition, such respiratory motion phantoms may typically be stand-alone devices lacking integration into the quality assurance procedures of the different parts and functions of the radiotherapy device. Such respiratory phantoms may comprise sensors indicating their location and/or current dimensions, which add further cost and engineering complexity. Example motion phantoms suitable for QA of a radiotherapy device include the ZEUS: Motion Management QA Phantom and the QUASAR™ MRI4D Motion Phantom.

SUMMARY

According to an aspect, there is provided a quality assurance method for a radiotherapy device, the method comprising: disposing a phantom on a patient couch of the radiotherapy device; moving the patient couch to simulate motion of a subject; determining a measured value associated with the phantom; and comparing the measured value to an expected value.

According to a further aspect, there is provided a radiotherapy device comprising: a radiation source configured to apply a radiation beam; a patient couch; a phantom disposable on the patient couch; and a controller (or controller circuitry) communicatively coupled to the patient couch, the controller being configured to: transmit a computer-executable instruction to the patient couch to cause it to simulate motion of a subject; determine a measured value associated with the phantom; and compare the measured value to an expected value.

According to a further aspect, there is provided a computer-readable medium (a non-transitory computer-readable medium) storing instructions which, when executed by a processor, cause the processor to: transmit a computer-executable instruction to a patient couch of a radiotherapy device to cause the patient couch to simulate motion of a subject, the patient couch having a phantom disposed thereon; determine a measured value associated with the phantom; and compare the measured value to an expected value.

According to a further aspect, there is provided a phantom for a radiotherapy device, the phantom comprising a fluid-filled tube containing a ball, the tube being oriented to be non-parallel and non-perpendicular to sides of the phantom along at least a part of the length of the tube.

BRIEF DESCRIPTION OF THE DRAWINGS

Specific embodiments are now described, by way of example only, with reference to the drawings, in which.

DETAILED DESCRIPTION

In radiotherapy, quality assurance (QA) is necessary to verify that a radiotherapy device is operating as expected within tolerances. For example, dosimetric QA involves verifying that the dose delivered is consistent with the dose calculated by the treatment plan. This may be verified by measuring the dose recorded by a film in a phantom. Since real subjects may move during a radiotherapy treatment, for example due to respiratory motion, cardiac motion, or peristalsis, it is desirable to verify that the radiotherapy device will operate as expected under these conditions. For example, it is desirable to verify that the dose delivered to a target during a gated or tracked treatment is consistent with that expected from the treatment plan. '4D' respiratory motion phantoms, which change their dimensions to replicate the motion of a subject as a function of time, are complex and expensive devices relative to static 3D phantoms. According to the techniques described herein, a phantom, i.e. a 3D phantom, can be disposed on the patient couch of a radiotherapy device, and the patient couch can be moved in a manner that simulates motion of a subject. For example, the couch may be programmed to move through a sinusoidal waveform to replicate respiratory motion. A measured value associated with the phantom, for example a dose measured by the phantom, may be determined and compared to an expected value, for example a dose according to the treatment plan. This can be used to perform motion-related QA for gated/tracked deliveries in an integrated and automated way while reducing the engineering complexity of required devices.

Figure 1:
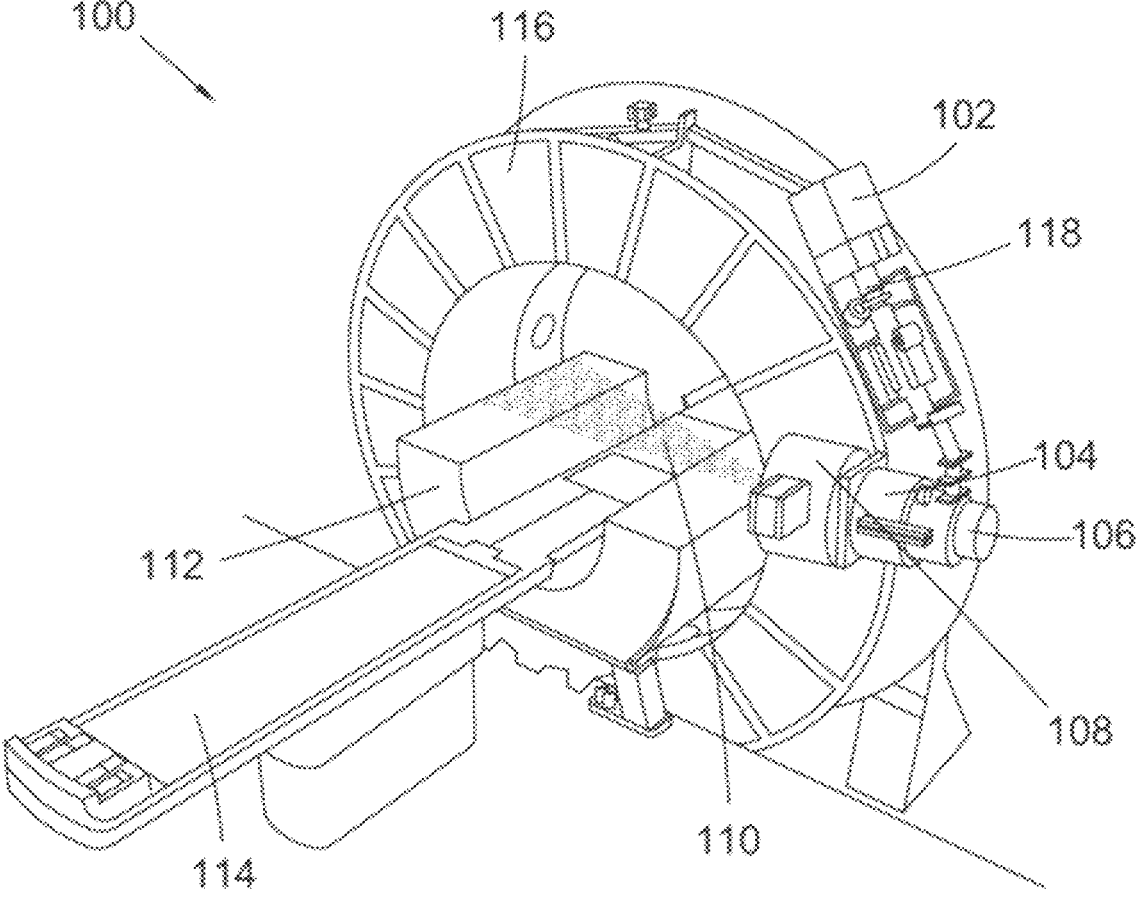
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present disclosure. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller. As used herein, a controller may also be referred to as a control device.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move to different positions including a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by one or more subject support surface actuators, which may be described as an actuation mechanism. The actuation mechanism is configured to move the subject support surface at least in a direction parallel to, and defined by, the central axis of the bore. The terms subject and patient are used interchangeably herein such that the patient support surface can also be described as a subject support surface. The subject support surface may also be referred to as a moveable or adjustable couch or table or as a patient couch or subject couch.

The radiotherapy apparatus/device depicted in FIG. 1 also comprises MR imaging apparatus 112. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller. While the discussion herein may focus on MR imaging by way of example, alternatively or in addition to MR imaging, one or more other imaging techniques, modalities, sensors or detectors may be used, such as CT/X-ray, PET, optical imaging/cameras, infra-red imaging, ultra-sound imaging or time-of-flight techniques. Any one or more of these may be used to determine the position of the target. As used herein, references to determining the position of the target may be used interchangeably with determining the position of the subject or of a part of the subject.

The controller is a computer, processor, or other processing apparatus. The controller may be formed by several discrete processors; for example, the controller may comprise a processor for each of the various individual components of the radiotherapy device as described herein. The controller is communicatively coupled to a memory, e.g. a computer readable medium. The controller may be communicatively coupled to one, multiple or all of the various individual components of the radiotherapy device as described herein. As used herein, the controller may also be referred to as a control device.

The linac device also comprises several other components and systems as will be understood by the skilled person. For example, in order to ensure the linac does not leak radiation, appropriate shielding is also provided.

The radiotherapy device and/or the control device may be configured to perform any of the method steps presently disclosed and may comprise computer executable instructions which, when executed by a processor cause the processor to perform any of the method steps presently disclosed, or when executed by the control device cause the control device to perform any of the method steps presently disclosed, or when executed by the radiotherapy device cause the radiotherapy device to perform any of the method steps presently disclosed. Any of the steps that the radiotherapy device and/or the control device is configured to perform may be considered as method steps of the present disclosure and may be embodied in computer executable instructions for execution by a processor. A computer-readable medium may comprise the above-described computer executable instructions.

Figure 2:
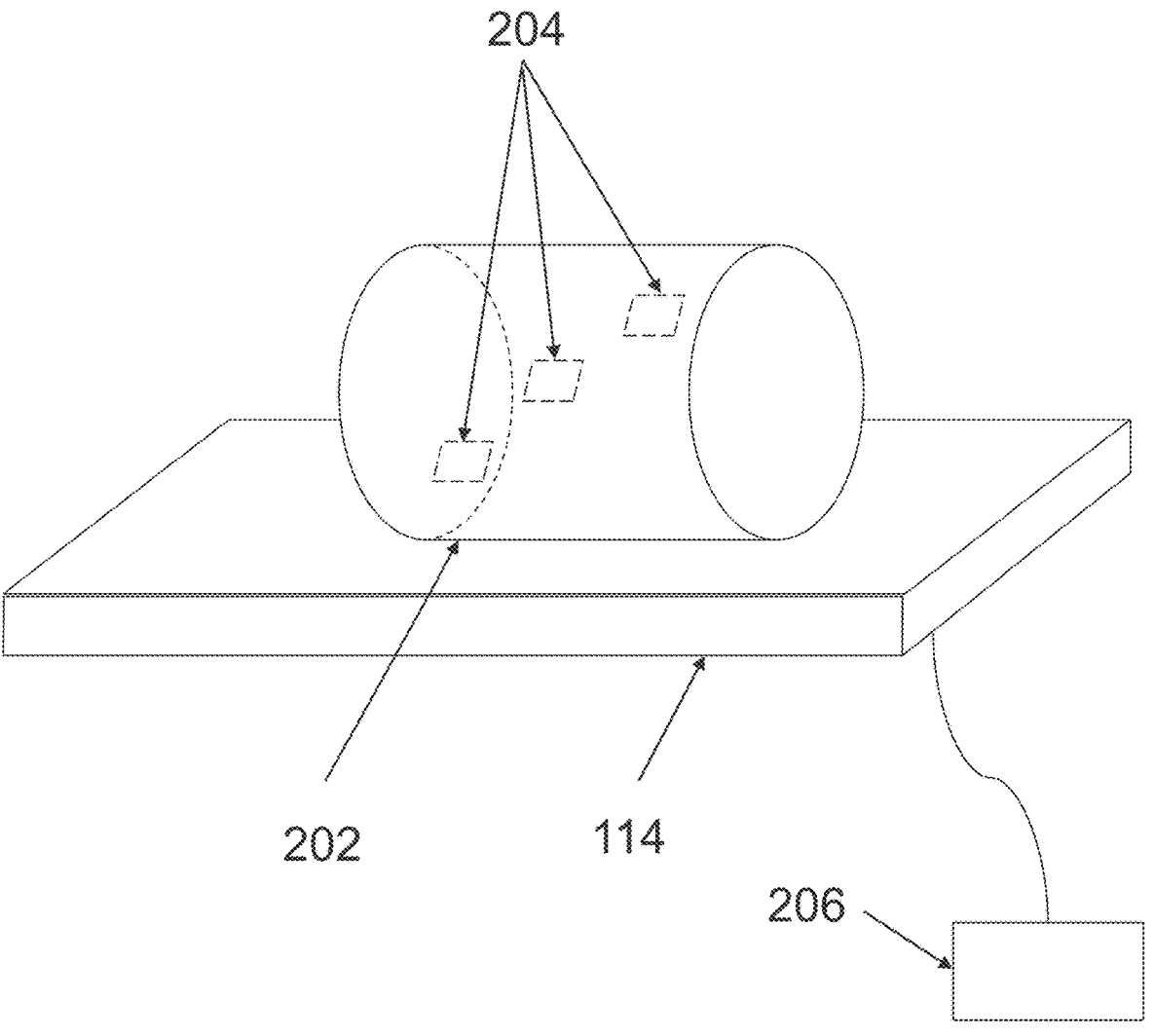
FIG. 2 depicts an example of a phantom according to the present disclosure.

FIG. 2 depicts an example of a phantom 202 according to the present disclosure. The phantom 202 is depicted as being disposed on the patient positioning surface or patient couch 114. In some examples, the phantom 202 may be fixed on the patient couch 114, for example in a particular location or orientation, using one or more accessories, mountings or fixation devices. The phantom 202 and the patient couch 114 may have cooperating features for fixing the phantom 202 in place on the patient couch 114. In other examples, the phantom 202 may simply be placed on the patient couch 114.

The phantom 202 may be considered to be a substitute for or a physical model of a subject's body or a part of a subject's body. The phantom 202 may not be a subject or a patient or a human or animal or a part thereof. The body of the phantom 202 may be formed of plastic, wood, or any other suitable material. The phantom 202 may be 3D or substantially 2D, i.e. flat, in form. The phantom 202 may be a three-dimensional physical object that represents or corresponds to the anatomy of a region of interest of the subject. The phantom 202 may comprise a portion corresponding to a target, e.g. a tumour, of a subject and/or a portion corresponding to an organ at risk of the subject. In some examples, the phantom may have a regular or standard geometrical, three-dimensional shape, such as a cube, a cylinder, a cuboid or a sphere. In other examples, the phantom 202 may be shaped to correspond to the anatomy of the human body, for example the anatomy of a particular subject or an average anatomy of many subjects. While a cylindrical shape of phantom 202 is depicted in FIG. 2 as an example, it will be understood that the present disclosure is not limited to this particular form of phantom, but rather is applicable to phantoms in general.

The phantom 202 may comprise one or more materials that are detectable via MV (or kV) imaging, i.e. it may be an MV (or kV) phantom. This material may be a dense material adequate for blocking X-rays such that the material shows up on an MV/kV image relative to its surroundings. The material may be a ceramic. The phantom 202 may comprise one or more materials that are detectable via MR imaging, i.e. it may be an MR phantom. This material may be a material comprising a particular chemical makeup that is readily identifiable via MR imaging. The material may comprise hydrogen atoms or molecules comprising hydrogen atoms. The material may comprise water or MR oil. In some examples, the phantom 202 may comprise one or more materials that are detectable via MV (or kV) imaging, in addition to one or more materials that are detectable via MR imaging, i.e. it may be an MVMR phantom. This may enable more efficient and more accurate QA through testing different imaging devices of the radiotherapy device at the same time and through enabling comparison of measurements by different imaging devices of the radiotherapy device. In such examples, the phantom 302 may comprise a capsule of MR-detectable material, such as an MR oil, with a MV-detectable object, such as a ceramic ball, inside the capsule.

The location of the ceramic ball may be detectable using an MV imaging device. The location of the MR oil may be detectable using an MR imaging device.

The phantom 202 may comprise one or more materials having radiation absorption properties similar to or the same as those of anatomical structures in the region of interest, for example of a tumour or a particular organ. The materials may have similar densities to or the same densities as one or more anatomical structures in the region of interest of the subject. These features may enable more accurate determination of the radiotherapy dose that parts of a subject would experience.

The phantom 202 may comprise one or more dosimeters 204, such as electronic dosimeters, thermoluminescent dosimeters, dosimetric films, alanine pellets, gel dosimeters, etc. The one or more dosimeters 204 may be disposed, embedded or contained within the phantom 202, or disposed on the surface of the phantom 202. In some examples, the phantom 202 may comprise one or more accessible compartments each for receiving respective dosimeters 204. Inclusion of multiple dosimeters 204 may enable a spatially resolved radiation dose to be determined such to provide information on what doses different parts of a subject can be expected to receive. The dosimeters may be disposed in a regular pattern such as in a cubic or helical grid. Alternatively, the dosimeters may be disposed in a random pattern. Each of the one or more dosimeters may be configured to measure respective measured values of dose, for example with the phantom 202 disposed on the patient couch 114 while a radiotherapy treatment is delivered according to a treatment plan.

The patient couch 114 is movable. The patient couch 114 may be movable through translation and/or rotation. The patient couch 114 may be movable through translation along one, two or three linear dimensions. The patient couch 114 may be rotatable about one, two or three linear axes. The patient couch 114 may be movable with six degrees of freedom.

Movement of the patient couch 114 may be controlled by a controller 206 communicatively coupled to the patient couch 114. The controller 206 may be communicatively coupled to the patient couch 114 via a wired or wireless connection. The controller 206 may be configured to transmit one or more signals to the patient couch 114 to cause movement of the patient couch 114. The patient couch 114 may comprise one or more motors and/or actuators (not shown) configured to effect the motion of the patient couch 114. Remote control of the patient couch 114 may be provided by sending software commands to a controller of the patient couch 114, i.e. to a user-interface module, through relays. The controller 206 may be disposed in the treatment room and motion of the patient couch 114 may be controlled from within the treatment room via the controller 206. Alternatively, the controller 206 may be disposed outside the treatment room and motion of the patient couch 114 may be controlled from outside the treatment room, i.e. remotely, using the controller 206. The controller 206 may correspond to a controller of the radiotherapy device or may be a separate controller communicatively coupled to the controller of the radiotherapy device. The motion of the patient couch 114 may be automated. The controller 206 may transmit a signal to the patient couch 114 to cause it to move to particular positions or to move with a particular displacement at different times. In other words, the signal may comprise a time-dependent pattern of motion for the patient couch 114 to be effected in an upcoming period of time.

The patient couch 114 can be moved to simulate motion of a subject. This movement may correspond to any physiological movement pattern anticipated or measured in respect of a real subject. Examples include motion due to a subject's respiratory cycle, cardiac cycle, coughing, sneezing, peristalsis and all other voluntary or involuntary movements. In some examples, the motion may be along a superior-inferior axis of the radiotherapy device or of an intended position of a subject, i.e. along the axis of rotation of the rotatable gantry 116. This axis may correspond to a direction into and out of a bore of the radiotherapy device, or a direction between the head and feet of the subject. The motion may be controlled according to any signal transmitted from the controller.

The motion may be sinusoidal along the superior-inferior axis, i.e. the location of the patient couch 114 along the superior-inferior axis may be a sinusoidal function of time. This may be used to simulate respiratory motion of a subject, the principal component of which is along the superior-inferior axis. Amplitude of the motion may be adjusted to account for depth of breath, with greater amplitudes corresponding to deeper breaths and smaller amplitudes corresponding to shallower breaths. The frequency of the motion may be adjusted to account for breathing rate, with higher frequencies corresponding to faster breathing and lower frequencies corresponding to slower breathing. Alternatively or in addition to comprising a component along the superior-inferior axis, the motion may comprise a component perpendicular to the floor (i.e. vertically up/down) and/or a further component parallel to the floor (i.e. horizontally left/right). These components may have smaller amplitudes to the superior-inferior component. These components may have the same or similar frequency to the superior-inferior component. Alternatively or in addition, the motion of the patient couch 114 may comprise one or more rotational components in one or more of the three rotational degrees of freedom. These techniques may enable more accurate simulation of the motion, e.g. respiratory motion, of a subject.

Since the patient couch 114 is an integrated part of the radiotherapy device, controlling motion of the phantom 202 using motion of the patient couch 114 may provide more efficient, more accurate and/or more useful quality assurance. For example, performing the dosimetric quality assurance of the radiotherapy treatment with respiratory movement may be performed at the same time as performing quality assurance for the patient couch 114. The time-base of motion of the patient couch 114 may correspond to a time-base used by other parts of the radiotherapy device, such that the motion may be more readily and accurately applicable to other parameters of a treatment session or to the treatment plan. This may help to avoid inaccuracies due to interpolation of data from different sources.

The controller 206 may be configured to provide a log, record, readout or data file indicating the location of the patient couch 114 in three-dimensional space as a function of time. This may provide an independent measure of the location of the phantom 202 as a function of time for comparison with data from one or more imaging sensors of or surrounding the radiotherapy device, for example with data from a kV/MV imaging device and/or an MR imaging device and/or one or more time-of-flight cameras monitoring the real-time position of one or more surfaces of the phantom or the patient couch 114. This may enable comparison, cross-correlation or averaging to improve the accuracy with which locations of the phantom 204 are known. The location information for the patient couch 114 may advantageously be at a higher frequency than that available from the imaging sensors, which may rely on complex reconstructions of locations from the raw measurement data taken. The location information for the patient couch 114 may advantageously be more precise or more accurate or may have a higher resolution than the location information from the imaging sensors. Since motion of the phantom 202 is achieved through motion of the patient couch 114, no extraneous components are needed to effect movement of the phantom 202. Therefore, issues related to interoperability, obsolescence and clutter in the treatment room are avoided or reduced, which may be of particular importance since space may be limited in the treatment room.

The techniques described herein expand the capabilities and utility of patient couches 114. Patient couches 114 have typically been designed simply to move between particular points and stop, in particular to transfer a subject on the patient couch 114 between a setup position and a treatment position. The treatment position may be encircled within the gantry or at least may be closer to the gantry than the setup position. Thus, the purpose of a patient couch 114 has typically been simply to support the patient and transfer them between a location in which they can mount the patient couch 114 and a position in which they can be treated. This typical arrangement of patient couches 114 simply moving between a setup position and a treatment position and stopping may in part be based on the desire to avoid interoperability concerns between the patient couch 114 and other parts of the radiotherapy device. For example, a patient couch 114 may be designed to only move in this way to avoid concerns relating to collisions with the bore of the radiotherapy device, the possibility for finger traps, and/or the need for additional safety engineering. Since the techniques described herein relate to quality assurance using a phantom, such safety-related concerns may be generally alleviated when using the techniques described herein. Through quality assurance using the phantom, it can be verified that a particular movement of the patient couch 114 is as expected and is safe for patient treatment. The techniques described herein provide more dynamic movement of a patient couch 114, for example to replicate a respiratory waveform of a subject. This enables a reduction in the number and complexity of devices required for QA of the radiotherapy device.

Application of radiation by a radiation source of a radiotherapy device in some time periods but not in others may be achieved by gating of a radiation beam emitted by the radiation source. The radiation source may comprise an electron source and a radiofrequency (RF) field source. The electron source may provide a source of electrons which generate a radiation dose to be delivered to the subject, for example by impacting a target. The RF field source may electromagnetically accelerate the electrons to a desired velocity suitable for providing the radiation dose. The radiation source may be gated by controlling the electron source to be on or off and/or by controlling the RF field source to be on or off. In this manner, application of a radiation dose by the radiation source can be controlled according to desired parameters.

Alternatively or in addition to gating of the radiation beam, tracking the radiation beam may be applied. Tracking involves responding to movement of a target by adjusting the location that is irradiated in dependence on the movement or time-varying position of the target. For example, a collimator, such as a multi-leaf collimator, may collimate and shape the radiation beam to direct it to up-to-date locations and/or spatial distributions of the target. Alternatively, or in addition, the patient couch 114 and/or the radiation source may be moved to track the movement or time-varying position of the target.

As will be appreciated, gating and tracking may be considered techniques for delivering a prescribed dose of radiation that take into account that the subject or a part thereof may move during a treatment session. Due to the additional variables involved for such treatments, e.g. relating to movement of the subject and one or more components of the radiotherapy device, it may be particularly important to verify that the gating and/or tracking is successful in delivering the prescribed doses of radiation to specified regions. The techniques described herein provide more efficient techniques for performing such quality assurance.

Figure 3:
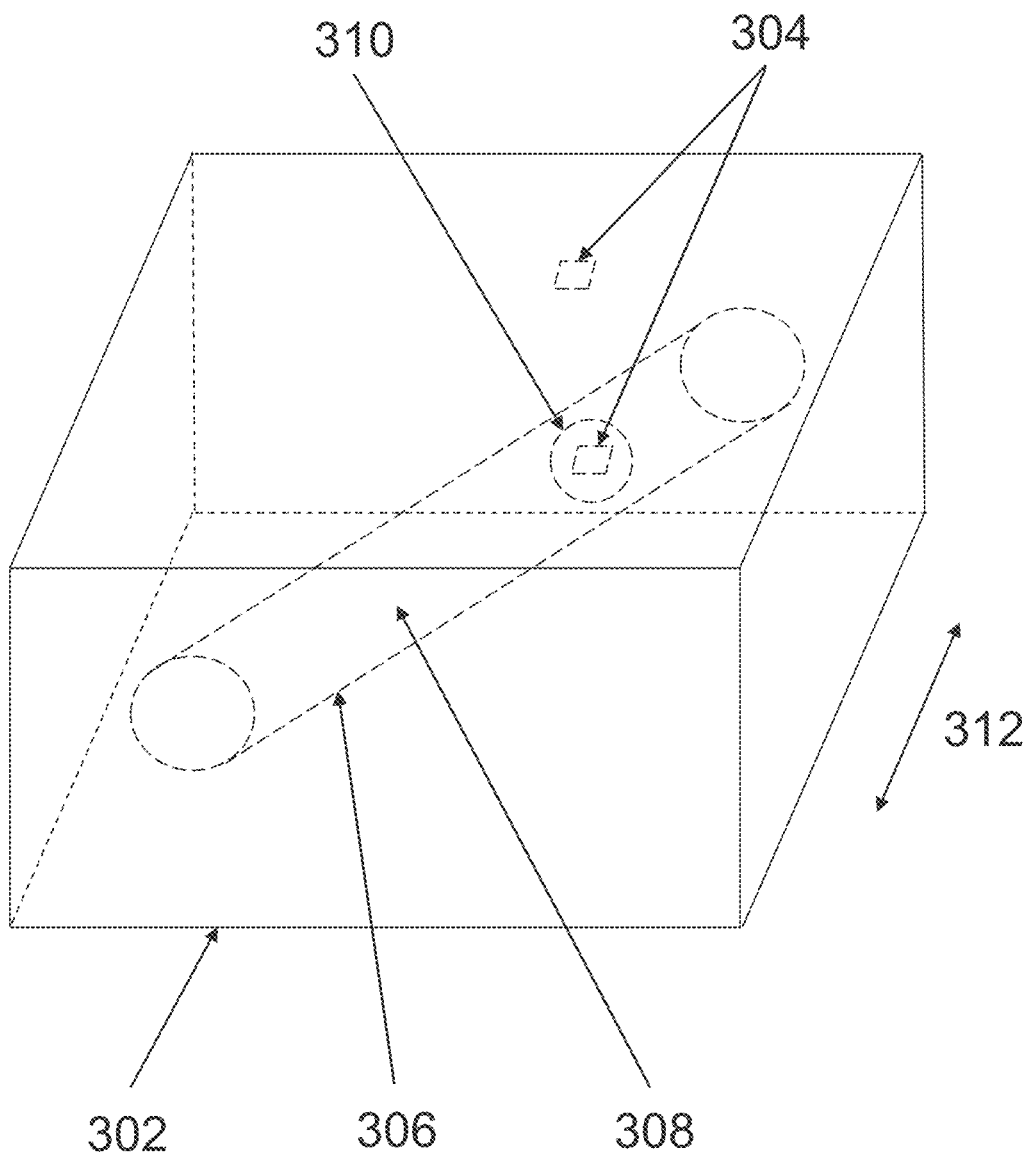
FIG. 3 depicts another example of a phantom according to the present disclosure.

FIG. 3 depicts another example of a phantom 302 according to the present disclosure. The phantom 302 is depicted as being cuboid in shape by way of non-limiting example. Other shapes are possible and contemplated, including the cylindrical shape of FIG. 2. The features and techniques described in relation to FIG. 2 are combinable with the features and techniques described in relation to FIG. 3, and vice versa. The points of difference will be focused on below to avoid repetition.

While translation and rotation of the patient couch 114 in six degrees of freedom has been described above in relation to FIG. 2, some radiotherapy devices may not be configured or arranged to effect motion of the patient couch 114 in all of these six degrees of freedom. For example, some radiotherapy devices may be configured to effect motion of the patient couch 114 only by way of translation along the superior-inferior axis. For such radiotherapy machines, it may be difficult to test motion components that do not align with this superior-inferior axis.

The above-mentioned issue is addressed by the phantom 302 depicted in FIG. 3. The phantom 302 comprises a tube or cavity or snake run 306. The tube 306 may be embedded within or bored through the phantom 302. The tube 306 may have a circular cross-section. The tube 306 may be generally cylindrical in shape. The tube 306 may contain or be filled with a fluid 308. One or more balls, spheres or ball-bearings 310 may be disposed within the tube 306. The ball(s) 310 may be immersed, surrounded or suspended in the fluid 308. In some examples, one or more dosimeters 304 may be disposed within the phantom 302. One or more dosimeters 304 may be disposed, contained or embedded within the body of the phantom 304 outside of the tube 306. One or more dosimeters 304 may be disposed, contained or embedded within the ball(s) 310.

In the example depicted in FIG. 3, the phantom 302 may again be disposed on a patient couch 114. The patient couch 114 may be configured to move along the superior-inferior axis, aligned with direction 312 as depicted in FIG. 3. In other words, the movement of the patient couch 114 may cause the phantom 302 to move forwards and backwards as depicted in FIG. 3. The tube 306 may be oriented diagonally with respect to the superior-inferior axis and/or with respect to the sides of the phantom 302. In other words, the tube 306 may be oriented to be non-parallel (and non-perpendicular) to the sides of the phantom 302 along at least a part of the length of the tube 306. In other words, the tube 306 may be oriented to deviate from the superior-inferior axis of the radiotherapy device along at least a part of the length of the tube 306 when the phantom 302 is disposed on the patient couch 114.

Movement of a single ball 310 will be considered below for each of explanation, though it will be understood that the described techniques are also applicable to multiple balls

310. The ball 310 may be caused to move along the length of the tube 306 due to the action of one or more forces. This movement may be effected by gravity, i.e. by the tube 306 having an upward-downward tilt, i.e. with respect to the floor of the treatment room and/or the upper and lower surfaces of the phantom 302. The movement may be caused by one or more springs or actuators within the tube 306. The movement may be caused by movement of the patient couch 114. The movement may be caused by electronic control, for example using an electronic motor. The movement of the ball 310 will have a component along the superior-inferior axis, but will also have a component along a different axis due to the orientation of the tube 306, i.e. an orthogonal component. The combination of movement of the patient couch 114 (along the superior-inferior axis), and movement caused by one or more of the forces described above (along the anterior-posterior axis and/or the medial-lateral axis) may provide 4D control of the location of the ball 310. In the example shown in FIG. 3, the movement of the ball 310 will have a component in the left-right (medial-lateral) direction since the tube 306 is generally oriented between a front left region of the phantom 302 and a back right region of the phantom 302. The fluid 308 may be selected to have a viscosity such that motion of the ball 310 is damped. The orthogonal component of motion may be determined from the inertia of the ball 310, which may be calculated from a series of images measured by one or more of sensors or imaging devices of the radiotherapy device. The orthogonal component may be determined from the inertia of the ball 310 as the patient couch 114 translates along the superior-inferior axis.

While the tube 306 depicted in FIG. 3 is oriented diagonally from a front left region of the phantom 302 to a back right region of the phantom 302, other orientations are considered and within the scope of the present disclosure. The tube 306 may be oriented diagonally from a front right region of the phantom 302 to a back left region of the phantom 302. The tube 306 may be tilted between the upper and lower surfaces of the phantom 302. The tube 306 may have one or more curves, undulations or zig-zags in two or three spatial dimensions within the phantom 302. Different shapes of tube 306 may be used to test different components of motion and/or different types of simulated movement. In some examples, the dimensions and/or orientation of tube 306 may be implemented in a manufacturing process of the phantom 302 based on measurements of motion of a particular subject or part of a subject, for example to capture their respiratory motion. In some examples, the phantom 302 may comprise multiple tubes 306 each including respective fluid 308 and one or more respective balls 310. The tubes 306 may have the same orientations and shapes, i.e. be parallel along their lengths or have the same form along their lengths, to enable multiple measurements to be taken and thereby improve accuracy through averaging. The tubes 306 may have different orientations and/or shapes in order to simultaneously and more efficiently test different components of motion.

Figure 4:
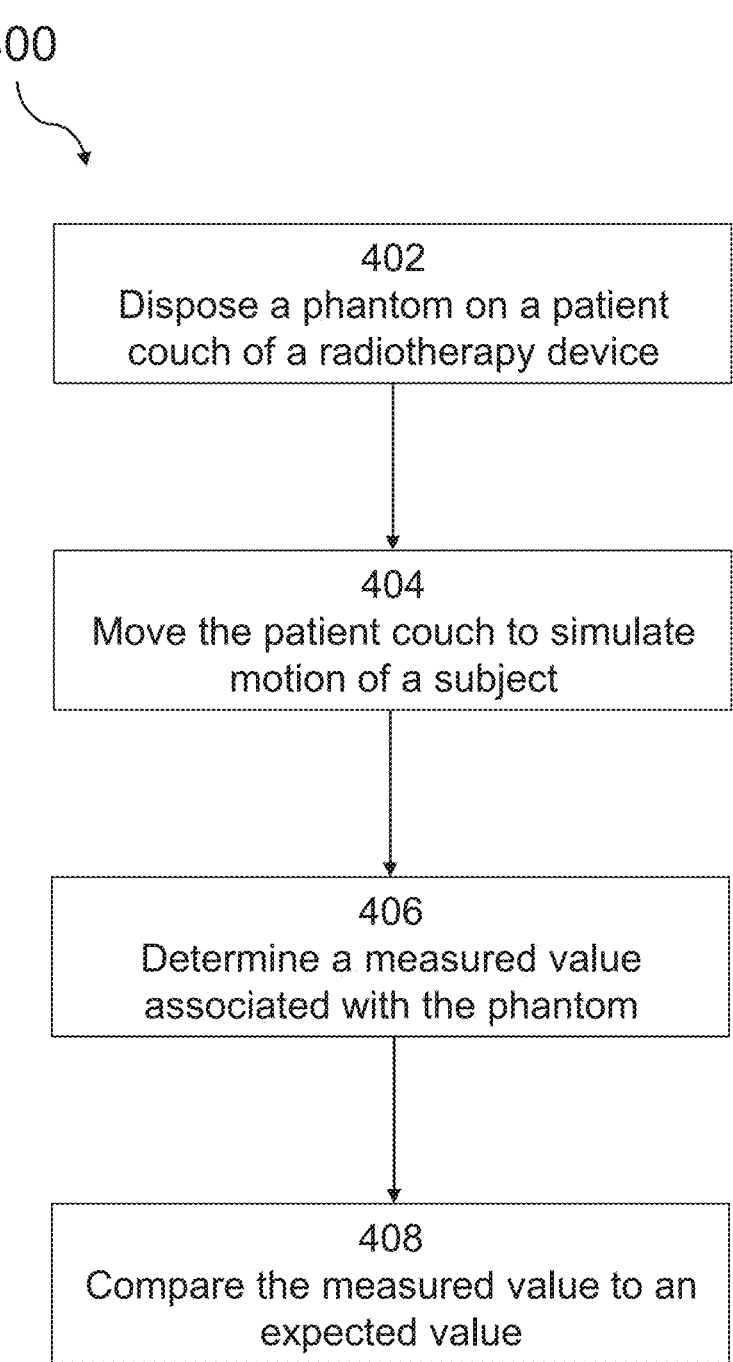
FIG. 4 depicts a method according to the present disclosure.

FIG. 4 depicts a method 400 according to the present disclosure. The method 400 in FIG. 4 is a quality assurance method for a radiotherapy device.

In a step 402, a phantom 202, 302 may be disposed on a patient couch 114 of a radiotherapy device. The patient couch 114 and/or the phantom 202, 302 may be configured to effect coupling between the patient couch 114 and the phantom 202, 302, for example via a first coupling device of the patient couch 114 and/or a second coupling device of the phantom 202, 302. Such coupling, or fixing, may avoid unintended movements of the phantom 202, 302, for example when the patient couch 114 is caused to move, and may fix the phantom 202, 302 with respect to the patient couch 114 in a particular position and/or a particular orientation. In other examples, the phantom 202, 302 may simply be placed on the patient couch 114. The patient couch 114 may comprise one or more locating features or markers to enable accurate placing of the phantom 202, 302 in an intended location and/or an intended orientation.

In a step 404, the patient couch 114 may be moved to simulate, mimic, imitate or replicate motion of a subject. The step 404 may be performed with the phantom 202, 302 disposed on the patient couch 114. In other words, the patient couch 114 may be moved such that the phantom 202, 302 disposed on the patient couch 114 moves in a corresponding or similar way to the way a subject disposed on the patient couch 114 would move. The motion may be sinusoidal along the superior-inferior axis, i.e. the location of the patient couch 114 along the superior-inferior axis may be a sinusoidal function of time. This may be used to simulate respiratory motion of a subject, the principal component of which is along the superior-inferior axis when the subject is lying on the patient couch 114. The motion may comprise a component perpendicular to the floor (i.e. vertically up/down) and/or a further component parallel to the floor (i.e. horizontally left/right). These components may have smaller amplitudes to that of the superior-inferior component. Alternatively or in addition, the motion of the patient couch 114 may comprise one or more rotational components in one or more of the three rotational degrees of freedom. These techniques may enable more accurate simulation of the respiratory motion of the subject. The motion of the patient couch 114 may alternatively or in addition simulate other movements of the subject, for example cardiac motion or involuntary, irregular movements such as those due to coughing or sneezing. Quality assurance taking into account cardiac motion may be particularly useful for treating targets near the heart. Quality assurance taking into account involuntary, irregular movements may be useful in testing how well the gating or tracking algorithms mitigate such movements in pausing or adjusting treatment.

The patient couch 114 may be moved in an automated manner, for example according to a programmed pattern of motion defining positions as a function of time, which may be predetermined in advance of movement of the patient couch 114. The patient couch 114 may be moved remotely, for example via a controller 206 located in a control room outside the treatment room.

In a step 406, a measured value associated with the phantom 202, 302 may be determined. The step 406 may be performed with the phantom 202, 302 disposed on the patient couch 114 or after the phantom 202, 302 has been removed from the patient couch. The measured value may be a radiation dose recorded by a dosimeter 204, 304, e.g. a dosimetric film, of the phantom 202, 302. In some examples, a plurality of measured values may be determined, for example by a plurality of dosimeters 204, 304, e.g. a plurality of dosimetric films, of the phantom 202, 302. This may enable a spatially-resolved distribution of delivered dose to be determined.

The measured value may be a location of the phantom 202, 302 at a particular timepoint. The location may be measured by one or more sensors or detectors, such as an MR imaging device and/or an MV/kV imaging device and/or one or more cameras (e.g. one or more time-of-flight cameras). In some examples, a time-resolved location of the phantom 202, 302 may be determined, i.e. a location of the phantom 202, 302 as a function of time. The time-resolved location may comprise a motion waveform for a motion-monitoring algorithm.

In a step 408, the measured value may be compared to an expected value. In examples in which the measured value is a radiation dose recorded by a dosimeter, the expected value may be a radiation dose included in a treatment plan. This treatment plan may specify a radiotherapy treatment through specifying positions and operations of one or more components of the radiotherapy device. The measured value may have been determined following or based on simulation of a radiotherapy treatment according to the treatment plan. The radiation dose included in the treatment plan may be a clinically prescribed dose for treating a target, i.e. a tumour. The radiation dose may be a dose which can be applied to an organ at risk without substantial safety risks, i.e. it may be used to verify than an intended treatment does not cause a dose above this level. In some examples, the treatment plan may include a plurality of the expected values, for example at different spatially-resolved locations. In such examples, these may be compared to respective ones of the plurality of measured values obtained from different dosimeters 204, 304 of the phantom 202, 302.

In examples in which the measured value is a location of the phantom 202, 302 at a particular timepoint, measured by one or more sensors or detectors, the expected value may be a location of the patient couch 114 at a same, similar or corresponding timepoint. This expected location may be determined based on movement of the patient couch 114. For example, the expected location may be determined from a programmed motion of the patient couch 114, or from a log, record, readout or data file indicating the location of the patient couch 114 as a function of time. A particular timepoint for the location of the patient couch 114 may be selected based on the timepoint of the measured value, or the timepoint of the measured value may be selected based on the timepoint for the location of the patient couch 114. This selection may be made through selecting a same time, or through selecting a closest time based on minimising the absolute difference between a particular timepoint and a series of timepoints. The expected value may be determined through interpolation of a series of expected values based on the timepoint of the measured value, or the measured value may be determined through interpolation of a series of measured values based on the timepoint of the expected value.

In some examples, the expected value may comprise a time-dependent location of the patient couch 114, i.e. the location of the patient couch 114 as a function of time. The time-resolved location may comprise a motion waveform. In such examples, the location of the phantom 202, 302 as a function of time as measured by the one or more imaging devices may be compared to the location of the patient couch 114 as a function of time based on the programmed pattern of motion or the readout of the motion of the patient couch 114. The comparison may be made through any suitable statistical techniques as would be familiar and accessible to the skilled person. The comparison of the expected value and the measured value may be used to verify a motion-monitoring algorithm, which may for example be used to inform gating or tumour tracking decisions by the radiotherapy device or the controller thereof.

The comparison between the location of the phantom 202, 302 and the location of the patient couch 114 may take into account the size and shape of the phantom 202, 302 and of the patient couch 114. In other words, since the phantom 202, 302 is disposed on the patient couch 114, and since each have a non-zero size, a location of the phantom 202, 302 and a location of the patient couch 114 may not exactly correspond, unless the upper surface of the patient couch 114 and the lower surface of the phantom 202, 302 are selected as the reference points for the comparison. The offset between the locations may be known or measured and accounted for in the comparison, for example by subtracting it from the differences in the locations.

In some examples, a comparison of measured and expected values comprising respective radiation doses and a comparison of measured and expected values comprising respective locations may both be performed. These two comparisons may be combined in a single instance of method 400, i.e. a single instance of step 404 of moving the patient couch may be used for both comparisons. This may further increase the efficiency of QA of a radiotherapy device.

The comparison of the measured value to the expected value may comprise taking the difference or absolute difference between the measured value and the expected value. This may be compared to a threshold. The threshold may be predetermined based on machine tolerances and/or safety tolerances which are clinically prescribed, for example in a treatment plan. Where the comparison comprises comparison of a measured dose and an expected dose, the threshold may be a dose difference, e.g. a margin corresponding to an acceptable deviation from the expected dose. Where the comparison comprises comparison of a measured location and an expected location, the threshold may be a distance or displacement that is acceptable for delivering an intended treatment, which may itself be calculated based on the dose distribution to be applied and/or the anatomy of a subject. Where the comparison comprises comparison of both dosimetric and geometrical information, a Gamma analysis may be applied and the threshold may be based on the associated Gamma pass-rate.

If the difference, or absolute difference, does not exceed the threshold, the quality assurance may be considered complete, at least in respect of the measured value and the expected value considered. If the difference, or absolute difference, does exceed the threshold, an indication or alert may be provided to notify a technician of this result. In response, a machine parameter and/or the treatment plan may be adjusted. In some examples, method 400 may then be repeated to verify if the difference between the measured value and the expected value does not exceed the threshold following the adjustment.

In some examples, sequential test automation may be performed according to the described techniques. A plurality of phantoms may be disposed on the patient couch 114 in different locations, for example at different locations along the superior-inferior axis. An automated step-and-test workflow may be implemented to sequentially perform QA using or based on each of the phantoms in turn, for example to determine if a delivered dose is consistent within an expected dose within a threshold and/or to determine if a location of the respective phantom or one or more features thereof is as expected within a threshold. For example, a periodic image quality test (PIQT) phantom may be disposed at a first location on the patient couch 114, and a MRMV phantom may be disposed at a second location on the patient couch 114. The patient couch 114 may be controlled to move, e.g. via the controller 206, such that the PIQT phantom is remotely translated to a predetermined location with respect to one or more components of the radiotherapy device, e.g. to the MR or MV isocentre. A PIQT test may be performed with the patient couch 114 and the PIQT phantom in this position. Next, the patient couch 114 may be controlled to move, e.g. via the controller 206, such that the MRMV phantom is remotely translated to the predetermined location with respect to one or more components of the radiotherapy device, e.g. to the MR or MV isocentre. A MRMV alignment test may be performed with the patient couch 114 and the MRMV phantom in this position. These techniques May further improve the efficiency of QA through enabling tests to be performed using different phantoms in quick succession as part of an automated workflow. These may test different components and different parameters of the radiotherapy device and/or different physical quantities. Moreover, since the tests may be performed as part of the same automated workflow without adjustment of other machine components in between, inadvertent changes in conditions or machine parameters may be avoided such that the results from the tests can be directly inter-related and compared without loss of accuracy.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

Figure 5:
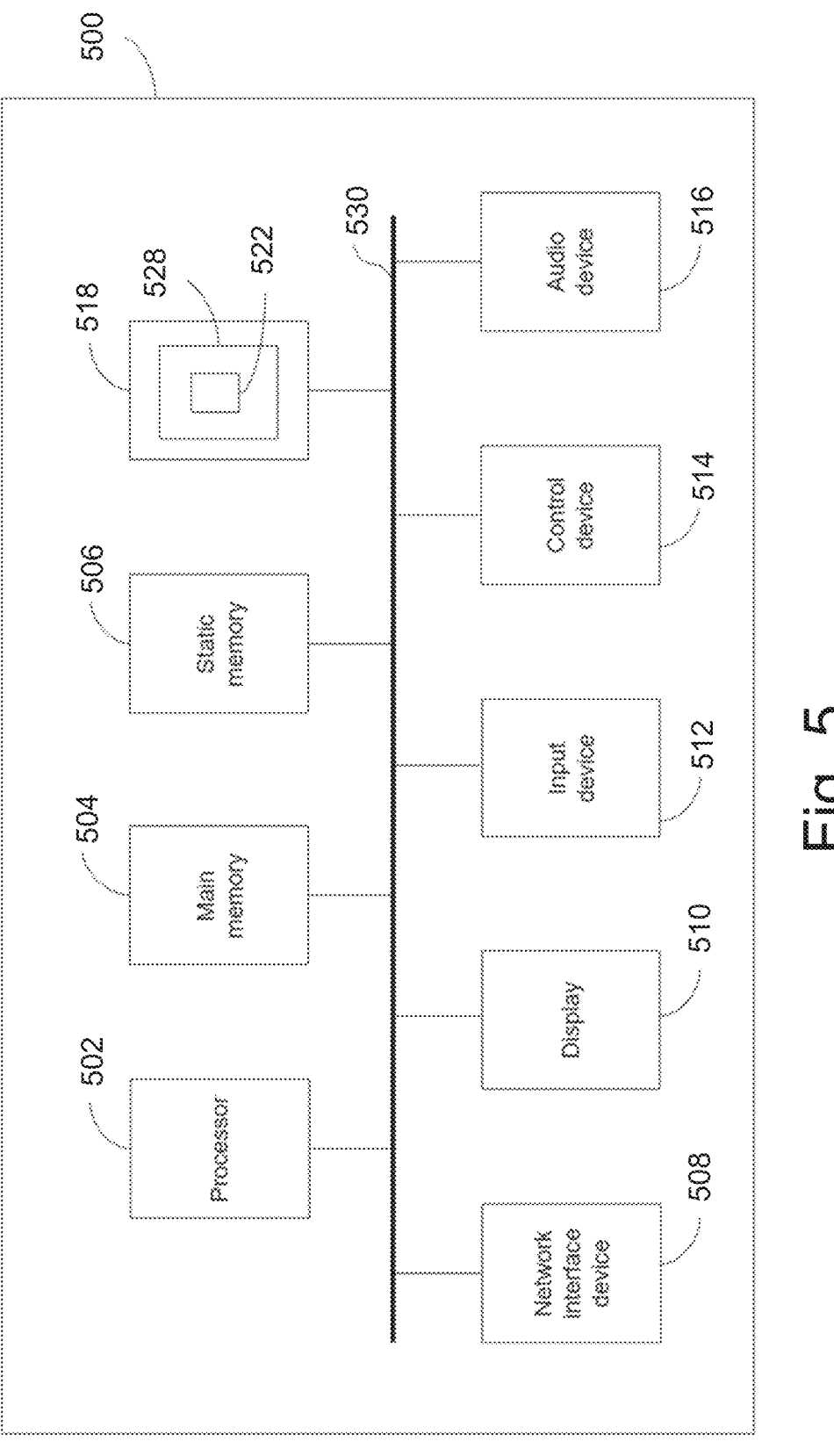
FIG. 5 depicts an example implementation of a computing device according to the present disclosure.

FIG. 5 illustrates a block diagram of one implementation of a computing device 500 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein. The computing device 500 may correspond to any one or more of the controllers or control devices described herein.

The example computing device 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a secondary memory (e.g., a data storage device 518), which communicate with each other via a bus 530.

Processing device 502 represents one or more general-purpose processors such as a microprocessor, central processing unit, or the like. More particularly, the processing device 502 may be a complex instruction set computing (CISC) microprocessor, reduced instruction set computing (RISC) microprocessor, very long instruction word (VLIW)

microprocessor, processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. Processing device 502 is configured to execute the processing logic (instructions 522) for performing the operations and steps discussed herein.

The computing device 500 may further include a network interface device 508. The computing device 500 also may include a video display unit 510 (e.g., a liquid crystal display (LCD) or a cathode ray tube (CRT)), an alphanumeric input device 512 (e.g., a keyboard or touchscreen), a cursor control device 514 (e.g., a mouse or touchscreen), and an audio device 516 (e.g., a speaker).

The data storage device 518 may include one or more machine-readable storage media (or more specifically one or more non-transitory computer-readable storage media) 528 on which is stored one or more sets of instructions 522 embodying any one or more of the methodologies or functions described herein. The instructions 522 may also reside, completely or at least partially, within the main memory 504 and/or within the processing device 502 during execution thereof by the computer system 500, the main memory 504 and the processing device 502 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The disclosure comprises the following items:

1. A quality assurance method for a radiotherapy device, the method comprising:
   disposing a phantom on a patient couch of the radiotherapy device;
   moving the patient couch to simulate motion of a subject;
   determining a measured value associated with the phantom; and comparing the measured value to an expected value.

2. A method according to item 1, comprising delivering a planned radiotherapy treatment to the phantom according to a treatment plan, wherein the measured value comprises a delivered dose to the phantom and the expected value comprises an expected dose from the treatment plan.

3. A method according to item 2, wherein the delivering of the planned radiotherapy treatment according to the treatment plan comprises delivering a gated treatment or a tracked treatment.

4. A method according to any preceding item, wherein the measured value comprises position data derived from an image of the phantom obtained from a sensor of the radiotherapy device, and the expected value comprises position data derived from a programmed movement of the patient couch.

5. A method according to any preceding item, wherein the patient couch is controlled to move to simulate breathing of the subject, comprising at least translating the patient couch along the superior-inferior axis of the radiotherapy device.

6. A method according to any preceding item, wherein the patient couch is controlled such that the location of the patient couch along the superior-inferior axis of the radiotherapy device is a sinusoidal function of time.

7. A method according to any preceding item, wherein the patient couch is controlled to be translated along and/or rotated around multiple degrees of freedom.

8. A method according to any preceding item, wherein the phantom comprises an MRMV phantom comprising at least a first material detectable using MV imaging and at least a second material detectable using MR imaging.

9. A method according to any preceding item, comprising disposing a plurality of phantoms on the patient couch, and, for each of the plurality of phantoms, moving the patient couch such that the respective phantom is in a predetermined location with respect to the radiotherapy device and performing quality assurance using the respective phantom in the predetermined location.

10. A method according to any preceding item, wherein the phantom comprises a fluid-filled tube containing a ball, the tube being oriented to deviate from the superior-inferior axis of the radiotherapy device along at least a part of its length when the phantom is disposed on the patient couch.

11. A method according to any preceding item, wherein the moving of the patient couch comprises remotely controlling the patient couch to move as a function of time according to an automated pattern of movement predetermined in advance of movement of the patient couch.

12. A radiotherapy device comprising:
   a radiation source configured to apply a radiation beam;
   a patient couch;
   a phantom disposable on the patient couch; and
   a controller communicatively coupled to the patient couch, the controller being configured to:
      transmit a computer-executable instruction to the patient couch to cause it to simulate motion of a subject;
      determine a measured value associated with the phantom; and
      compare the measured value to an expected value.

13. A radiotherapy device according to item 12, configured to deliver a planned radiotherapy treatment to the phantom according to a treatment plan, wherein the measured value comprises a delivered dose to the phantom and the expected value comprises an expected dose from the treatment plan.

14. A radiotherapy device according to item 13, wherein the delivering of the planned radiotherapy treatment according to the treatment plan comprises delivering a gated treatment or a tracked treatment.

15. A radiotherapy device according to any of items 12-14, wherein the measured value comprises position data derived from an image of the phantom obtained from a sensor of the radiotherapy device, and the expected value comprises position data derived from a programmed movement of the patient couch.

16. A radiotherapy device according to any of items 12-15, wherein the computer-executable instruction is configured to cause the patient couch to move to simulate breathing of the subject, comprising at least translating the patient couch along the superior-inferior axis of the radiotherapy device.

17. A radiotherapy device according to any of items 12-16, wherein the computer-executable instruction is configured to cause the patient couch to move such that the location of the patient couch along the superior-inferior axis of the radiotherapy device is a sinusoidal function of time.

18. A radiotherapy device according to any of items 12-17, wherein the computer-executable instruction is configured to cause the patient couch to translate along and/or rotate around multiple degrees of freedom.

19. A radiotherapy device according to any of items 12-18, wherein the phantom comprises an MRMV phantom comprising at least a first material detectable using MV imaging and at least a second material detectable using MR imaging.

20. A radiotherapy device according to any of items 12-19, comprising a plurality of phantoms disposable on the patient couch, wherein the controller is configured, for each of the plurality of phantoms, to effect movement of the patient couch such that the respective phantom is in a predetermined location with respect to the radiotherapy device and to perform quality assurance based on the respective phantom in the predetermined location.

21. A radiotherapy device according to any of items 12-20, wherein the phantom comprises a fluid-filled tube containing a ball, the tube being oriented to deviate from the superior-inferior axis of the radiotherapy device along at least a part of its length when the phantom is disposed on the patient couch.

22. A radiotherapy device according to any of items 12-21, wherein the controller is configured to control the patient couch to move as a function of time according to an automated pattern of movement predetermined in advance of movement of the patient couch.

23. A computer-readable medium storing instructions which, when executed by a processor, cause the processor to:

transmit a computer-executable instruction to a patient couch of a radiotherapy device to cause the patient couch to simulate motion of a subject, the patient couch having a phantom disposed thereon;

determine a measured value associated with the phantom; and compare the measured value to an expected value.

24. A phantom for a radiotherapy device, the phantom comprising a fluid-filled tube containing a ball, the tube being oriented to be non-parallel and non-perpendicular to sides of the phantom along at least a part of the length of the tube.

What is claimed is:

1. A quality assurance method for a radiotherapy device, the method comprising:

disposing a phantom on a patient couch of the radiotherapy device;

moving the patient couch to simulate motion of a subject;

determining a measured value associated with the phantom; and comparing the measured value to an expected value.

2. The method according to claim 1, comprising:

delivering a planned radiotherapy treatment to the phantom according to a treatment plan, wherein the measured value comprises a delivered dose to the phantom and the expected value comprises an expected dose from the treatment plan, and wherein the delivering of the planned radiotherapy treatment according to the treatment plan comprises delivering a gated treatment or a tracked treatment.

3. The method according to claim 1, wherein the measured value comprises position data derived from an image of the phantom obtained from a sensor of the radiotherapy device, and the expected value comprises position data derived from a programmed movement of the patient couch.

4. The method according to claim 1, wherein the patient couch is controlled to move to simulate breathing of the subject, comprising at least translating the patient couch along a superior-inferior axis of the radiotherapy device, wherein the superior-inferior axis is parallel or coincident with a longitudinal axis of the patient couch.

5. The method according to claim 1, wherein the patient couch is controlled such that a location of the patient couch along a superior-inferior axis of the radiotherapy device is a sinusoidal function of time, wherein the superior-inferior axis is parallel or coincident with a longitudinal axis of the patient couch.

6. The method according to claim 1, wherein the patient couch is controlled to be at least one of translated along or rotated around multiple degrees of freedom.

7. The method according to claim 1, wherein the phantom comprises an MRMV phantom comprising at least a first material detectable using mega-voltage (MV) imaging and at least a second material detectable using magnetic resonance (MR) imaging.

8. The method according to claim 1, comprising:

disposing a plurality of phantoms on the patient couch, and, for each respective phantom of the plurality of phantoms, moving the patient couch such that a particular respective phantom is in a predetermined location with respect to the radiotherapy device; and performing quality assurance using the particular respective phantom in the predetermined location.

9. The method according to claim 1, wherein the phantom comprises a fluid-filled tube containing a ball, the fluid-filled tube being oriented to deviate from a superior-inferior axis of the radiotherapy device along at least a part of a length when the phantom is disposed on the patient couch wherein the superior-inferior axis is parallel or coincident with a longitudinal axis of the patient couch.

10. The method according to claim 1, wherein the moving of the patient couch comprises remotely controlling the patient couch to move as a function of time according to an automated pattern of movement determined in advance of movement of the patient couch.

11. A radiotherapy device comprising:

a radiation source configured to apply a radiation beam;

a patient couch;

a phantom disposable on the patient couch; and controller circuitry communicatively coupled to the patient couch, the controller circuitry configurable to:

transmit a computer-executable instruction to the patient couch to cause the patient couch to simulate motion of a subject;

determine a measured value associated with the phantom; and compare the measured value to an expected value.

12. The radiotherapy device according to claim 11, wherein the controller circuitry is configurable to:

deliver a planned radiotherapy treatment to the phantom according to a treatment plan, wherein the measured value comprises a delivered dose to the phantom and the expected value comprises an expected dose from the treatment plan, and wherein the delivering of the planned radiotherapy treatment according to the treatment plan comprises delivering a gated treatment or a tracked treatment.

13. The radiotherapy device according to claim 11, wherein the measured value comprises position data derived from an image of the phantom obtained from a sensor of the radiotherapy device, and wherein the expected value comprises position data derived from a programmed movement of the patient couch.

14. The radiotherapy device according to claim 11, wherein the computer-executable instruction is configured to cause the patient couch to move to simulate breathing of the subject, comprising at least translating the patient couch along a superior-inferior axis of the radiotherapy device wherein the superior-inferior axis is parallel or coincident with a longitudinal axis of the patient couch.

15. The radiotherapy device according to claim 11, wherein the computer-executable instruction is configured to cause the patient couch to move such that a location of the patient couch along a superior-inferior axis of the radiotherapy device is a sinusoidal function of time wherein the superior-inferior axis is parallel or coincident with a longitudinal axis of the patient couch, and/or wherein the computer-executable instruction is configured to cause the patient couch to at least one of translate along or rotate around multiple degrees of freedom.

16. The radiotherapy device according to claim 11, wherein the phantom comprises an MRMV phantom comprising at least a first material detectable using mega-voltage (MV) imaging and at least a second material detectable using magnetic resonance (MR) imaging.

17. The radiotherapy device according to claim 11, comprising:
a plurality of phantoms disposable on the patient couch, wherein the controller is configured, for each respective phantom of the plurality of phantoms, to effect movement of the patient couch such that a particular respective phantom is in a predetermined location with respect to the radiotherapy device and wherein the controller circuitry is configurable to perform quality assurance based on the particular respective phantom in the predetermined location.

18. The radiotherapy device according to claim 11, wherein the phantom comprises a fluid-filled tube containing a ball, the fluid-filled tube being oriented to deviate from a superior-inferior axis of the radiotherapy device along at least a part of a length when the phantom is disposed on the patient couch, wherein the superior-inferior axis is parallel or coincident with a longitudinal axis of the patient couch.

19. The radiotherapy device according to claim 11, wherein the controller circuitry is configurable to:
control the patient couch to move as a function of time according to an automated pattern of movement determined in advance of movement of the patient couch.

20. A phantom for a radiotherapy device, the phantom comprising:
a fluid-filled tube containing a ball, the tube being oriented to be non-parallel and non-perpendicular to sides of the phantom along at least a part of a length of the tube.

* * * * *